Figure 1:
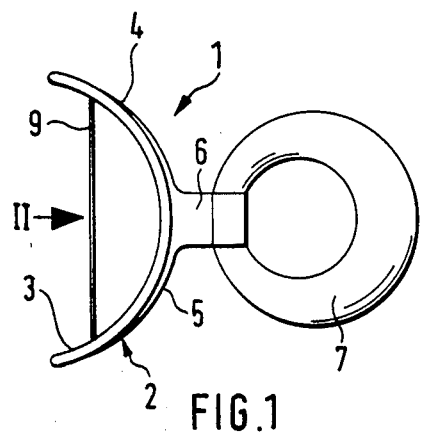

United States Patent [19]

Hinz

[11] Patent Number: 4,690,640
[45] Date of Patent: Sep. 1, 1987

[54] ORAL VESTIBULE PLATE FOR PROPHYLACTIC PURPOSES AND EARLY ORTHODONTIC TREATMENT

[76] Inventor: Relf Hinz, Kornerstrasse 6, D-4690 Herne 1, Fed. Rep. of Germany

[21] Appl. No.: 798,901

[22] Filed: Nov. 18, 1985

[51] Int. Cl.⁴ ............................................. A61C 7/00
[52] U.S. Cl. ........................................................ 433/6
[58] Field of Search ........................................ 433/5, 6

[56] References Cited

U.S. PATENT DOCUMENTS 2,880,509  4/1959  Strickler .................................. 433/5
4,179,811 12/1979  Hinz ....................................... 433/6

OTHER PUBLICATIONS

"Deutsche Stomalogie" 21 Mar. 1971 pp, 217–223 by Von E. Schonherr.

Professional Positioners, 4 pages, Post Office Box 1200, Enfield Conn,, 06082, Jan. 1974.
Descriptive literature showing the subject matter of U.S. Pat. No. 4,179,811 and the subject matter of the present application.
A letter and translation thereof from an East German dentist describing problems encountered with the prior art.

*Primary Examiner*—Robert Peshock
*Attorney, Agent, or Firm*—Andrus, Sceales, Starke & Sawall

[57] ABSTRACT

An oral vestibule plate for prophylactic purposes includes a curved rigid shield. A cross piece is disposed on the center plane of the shield along the secant of its curvature. The cross piece comprises a wire bent to hold back the tip of the tongue thereby preventing damage otherwise caused by the tongue.

8 Claims, 7 Drawing Figures

ORAL VESTIBULE PLATE FOR PROPHYLACTIC PURPOSES AND EARLY ORTHODONTIC TREATMENT

The present invention relates to an oral vestibule plate for prophylactic purposes and early orthodontic treatment of children, comprising a curved rigid plastic shield to be inserted in the oral vestibule, i.e. between the dental arches and the lips, the inside of which has a smooth design while the outside is provided with a holder for a ring which is linked to the holder and pivotable about an axis parallel to a tangent of the outer curvature of the shield, the holder protruding outwardly between the lips with the link of the ring when the shield is inserted.

That children suck in various ways is based on a natural need. This sucking is more or less pronounced. Thumbsucking generally leads to deformation of the curve of the teeth and thus to the so-called "open bite". The resulting damage consists in the possibility of insufficient chewing action and improper articulation during speech. The teeth of the upper jaw are frequently pushed forward out of their normal position. This may readily lead to obstruction of the child's nasal breathing and corresponding difficulties in breathing. At the same time, speech defects often occur. Prophylaxis should prevent too much damage from coming about as a result of children's sucking. Early orthodontic treatment should eliminate damage that has occurred before it can assume any larger proportions. At the same time, the child should be permanently cured of the habit of sucking.

The inventive oral vestibule plate differs from other apparatus of dental medicine which are always fitted individually to remove errors in the position of the teeth or abnormalities in the jaw, and have been offered up to now with the same dimensions due, for instance, to their industrial production in large numbers from plastic material, although more than one size, generally two, are available. The oral vestibule plate according to the invention is based on the forces triggered by sucking, i.e. on the sucking effect of this habit of children, who thereby press the oral vestibule plate against the dental arch. Inventive oral vestibule plates are thus products which, unlike so-called "orthodontic treatment apparatus", are used for prephylactic purposes for a great number of dental arch sizes and for early treatment for an even greater number of abnormalities of the dental arch faulty tooth positions.

Oral vestibule plates of this kind are used in pediatric dentristy because they do justice to children's natural need to such, i.e. they make use of the sucking, as long as it is not voluntarily abandoned, to prevent the damage it causes and eliminate abnormalities of the described kind. Furthermore, oral vestibule plates are reliable in their application unlike pacifiers, which also comply with children's natural need to suck. Thus, they generally do not require constant dental or orthodontic check-ups or care. This is especially so as the protruding ring of the oral vestibule plate can be used for improved handling of the plate and for myotherapy, if required.

The invention assumes a previously known oral vestibule plate of the type described at the outset (U.S. Pat. No. 4,179,811). This oral vestibule plate has a smooth inside on its shield. When the shield is properly placed behind the lips and in front of the anterior teeth, (front teeth) it is held in its proper position by the lip muscles. If the anterior teeth of the upper jaw protrude, the pressure is exerted thereon. This is pushing back the anterior teeth and puts them into their proper position. Experience shows that it is much easier to cure the sucking habit by wearing such an oral vestibule plate.

However, it is disadvantageous that a number of kinds of damage caused by particular sucking habits cannot be eliminated, or not eliminated optimally, by the previously known type of oral vestibule plate. An example of such damage is a distal placement of the lower dental arch (setback of which is usually caused by thumb-sucking). This kind of damage cannot be eliminated by the above-mentioned pressure against the front teeth of the upper jaw.

Another serious kind of damage is caused by so-called "tongue-pressing". The child presses its tongue between the teeth, which leads to an open bite of the anterior teeth, often arching the upper front teeth upwards. The use of the previously known oral vestibule plate does not correct this because it cannot rule out tongue-pressing.

The invention is based on the problem of providing an oral vestibule plate of the type described at the outset which in a simple manner prevents further damage from occurring due to tongue-pressing and can be used for successfully treating such damage with the aim of eliminating it.

The invention is also intended to provide an oral vestibule plate which, in spite of its special design, can still be produced industrially and requires only little adaption. In particular, two sizes of the oral vestibule plate should be sufficient in practice. At the same time, however, it should be possible to fit it to the individual tooth position without special measurements having to be made available.

The invention is further aimed at providing an oral vestibule plate which allows in a simple manner for correction of a distally placed lower jaw caused by sucking.

It is proposed for this purpose according to the invention that a crosspiece is disposed approximately on the center plane of the shield along a secant of its curvature, said crosspiece consisting of a wire with each of its ends introduced into a recess in the inside and sealed, and having aligned straight lengthwise portions proceeding from the two ends of the shield as well as a center portion in which the crosspiece wire describes at least one hairpin bend between one approximately sinusoidal curve on each side, the crosspiece serving the purpose of holding back the tip of the tongue by aid of its center portion.

The described crosspiece may be attached to a conventional oral vestibule plate in the dentist's or orthodontist's office by providing the recesses for the wire ends in the plate, inserting the crosspiece wire and attaching it with setting adhesive. On the other hand, the crosspiece may of course be attached to the oral vestibule plate from the beginning, this being offered as a special form.

The crosspiece is rigid enough that the tongue which hits it cannot press it forward. The crosspiece thus holds the tongue back from the teeth, thereby preventing the damage otherwise caused by the tongue. In particular, the special shape of the crosspiece ensures that the flow of saliva is not obstructed, on the one hand, but that the tip of the tongue hits the center portion, on the other hand, which consists of the hairpin portions projecting upward and downward particularly far. They are joined toward the outside by the portions of the wire not projecting out as far, thereby reducing the supporting effect and not obstructing the tongue along its edges.

It has become apparent that the described shape of the crosspiece not only prevents tongue-pressing but also cures this habit, whereby the effect of the oral vestibule plate is not inhibited, i.e. it comes to lie against the anterior teeth when sucked and returns them, and possibly the jaws, to their normal positions.

This embodiment of the inventive oral vestibule plate preferably involves both sinusoids pointing in the same direction and enclosing a pair of hairpin portions of the center portion pointing in the same direction and three hairpin portions pointing in the opposite direction. In this way the described effect can be optimally achieved.

Other features of the invention relating to embodiments of the inventive oral vestibule plate suitable for prophylactic purposes and the early orthodontic treatment of set-back lower jaws, involve a strip being provided on the back of the shield extending at right angles to the curved plane of the shield and extending on both sides of the vertical center plane of the shield in an arc corresponding to the anterior teeth of the lower jaw and formed of one piece with the shield and a flange fitting behind the anterior teeth of the lower jaw. This kind of oral vestibule plate is inserted in the usual manner. However, the cap consisting of the strip and the flange prevents the shield from tilting downward, as caused by the distal placement of the lower jaw. The cap therefore trains the forward shift of the lower jaw and facilitates closing of the lips.

In this embodiment the flange is preferably arranged in such a way as to form an obtuse angle with its underside and the underside of the strip, its free edge acquiring an arcuate recess. Consequently, when it is bitten into this exerts a forwardly pulling force on the lower jaw, which is desirable for correcting the lower jaw. The arcuate recess avoids pressure on the frenulum of the tongue.

This embodiment of the invention is generally designed further in such a way that the strip and the flange extend approximately across half the arc of the shield. This causes the correcting force to be exerted on the anterior teeth of the lower jaw, which are mainly affected by deformation.

The invention further involves at least the shield being made of a polystyrene plastic material and having a smooth surface structure by being molded in the die, the polystyrene material being deformable by being heated in hot water, making the shield capable of being adapted to the individual curve of the teeth, the polystyrene material being rigid at the average air temperature. In this way it is possible to individually fit the inventive oral vestibule plates produced industrially in two sizes, for example, by making the shield briefly deformable under very hot water, for example from a normal hot-and-cold water basin, and then allowing it to cool at the normal air temperature, whereby it resumes the rigidity required for the functioning of an oral vestibule plate.

Figure 2:
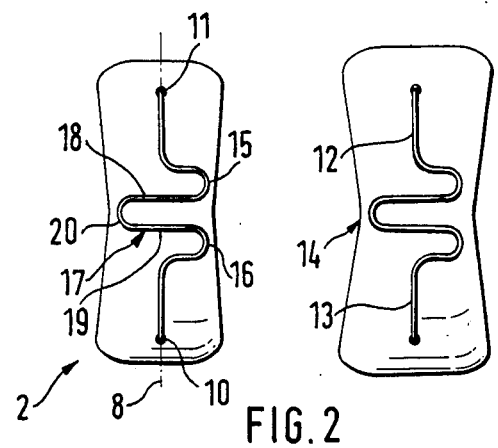

The details, further features and other advantages of the invention can be found in the following description of embodiments with reference to the figures in the drawing. These show:

FIG. 1 a first embodiment of the inventive oral vestibule plate seen from the top FIG. 2 a view in the direction of arrow II of FIG. 1, showing two sizes of the oral vestibule plate as in FIG. 1

Figure 3:
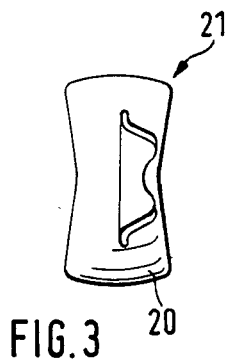

FIG. 3 a modified embodiment of the inventive oral vestibule plate in the view corresponding to FIG. 2

Figure 4:
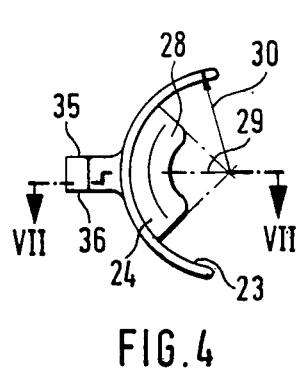

FIG. 4 the view of FIG. 3 seen from the top

Figure 5:
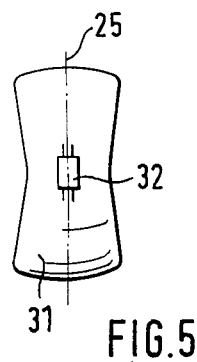

FIG. 5 the object of FIGS. 3 and 4 seen from the front

Figure 6:
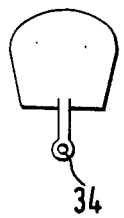

FIG. 6 the object of FIGS. 3 to 5 seen from the side

Figure 7:
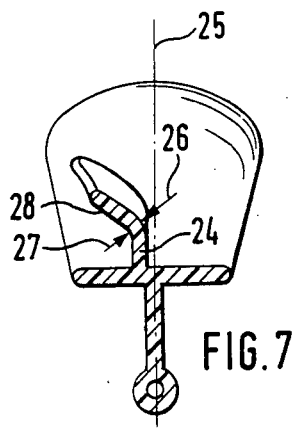

FIG. 7 a cross-section along line VII—VII of FIG. 4

The view of FIG. 1 shows the basic structure of the inventive oral vestibule plate. According thereto, the oral vestibule plate generally referred to as 1 has a curved rigid shield 2 made of plastic material, which shall be explained in more detail below. Inside 3 has a smooth design. Outside 4 bears an arcuate rib 5 from which a holder 6 protrudes. A ring 7 is pivotable on holder 6 about an axis parallel to a tangent of the outer curvature of the shield.

A crosspiece 9 is attached approximately on center plane 8 of shield 2 (FIG. 2) along a secant (FIG. 1) of its curvature. The crosspiece consists of a wire with each of its ends introduced into a recess, e.g. a bore, disposed at 10, 11 (FIG. 2) but not shown in more detail, on each side. The ends of the wire are sealed in the bores, which may be effected, for example, by setting plastic material. The wire itself consists of three lengthwise portions, i.e. two identical portions 12, 13 each proceeding from recess 10, 11, and a center portion 14. This center portion has two sinusoidal curves 15, 16 which project in the same direction. The two sinusoidal curves 15, 16 enclose a hairpin-shaped piece 17 exhibiting accordingly two substantially parallel straight arms 18, 19 and a connecting semicircular curve 20.

The oral vestibule plate shown in FIGS. 1 and 2 is for propyhlactic purposes and the early orthodontic treatment of children. For this purpose, the oral vestibule plate is inserted between the lips and the anterior teeth. Holder 6 protrudes outwardly between the lips. The readily rotatable ring 7 then hangs down. The tongue comes to lie in front of the center portion, i.e. parts 15 to 20 of crosspiece 9. This prevents the tip of the tongue from being pressed between the anterior teeth. This is one of the sucking habits of children.

Since the child initially continues sucking, the anterior teeth of the upper and lower jaws are pressed against shield 2 and thereby corrected.

The embodiment as in FIGS. 3 to 7 serves the purpose of correcting a set-back lower jaw. For this purpose, oral vestibule plate 21 (FIG. 3) has on its shield 22, i.e. on its inside 23 (FIG. 4), a strip 24 extending parallel to center plate 25. When the child has inserted oral vestibule plate 21, flange 24 is located below center plane 25. Strip 24 runs into a flange 28 via an outer radius 26, 27 in each case. The flange is downwardly curved in the assumed position of the oral vestibule plate. As indicated by the view in FIG. 4, the arrangement consisting of strip 24 and flange 28 occupies an arc angle of 90° extending on both sides of the vertical center plane 29 of the oral vestibule plate. The radius of curvature is recognizable at 30 in FIG. 4.

The oral vestibule plate again has on its outside 31 holder 32, which corresponds to the holder in the embodiment as in FIGS. 1 and 2. The ring is not shown which locks with protruding cams into recesses 34 on both sides 35, 36 of the holder.

The described oral vestibule plates are made of a polystyrene material which has a smooth surface structure by being molded in the die. The die has two parts and is divided on center plane 25. Thus, the dividing line of the die extends on this plane and causes no disturbance.

Polystyrene material is a thermoplast. This makes it possible to make the shield deformable by heating it in hot water so that it can be individually adapted. When cooled at normal air temperature, however, it becomes so rigid that the oral vestibule plate can no longer be deformed.

The oral vestibule plate as in FIGS. 3 to 7 is inserted between the lips and anterior teeth, i.e. in the so-called "oral vestibule", as described with reference to the embodiment of FIGS. 1 and 2. The child bites with the anterior teeth of his lower jaw onto flange 28, thereby drawing the oral vestibule plate against the anterior teeth. The reaction power shapes the lower jaw forwardly, thereby eliminating the described abnormality.

The described polystyrene material is mouth-resistant and safe for food. Its thermoplastic behavior, which has been described above, makes it possible to adapt industrially produced oral vestibule plates. Two sizes essentially sufficient their relative sizes being shown in FIG. 2.

I claim:

1. An appliance for prophylaxis and early orthodonic treatment of children, said appliance comprising:
   a curved, rigid shield of plastic material suitable for being inserted into the vestibule of the mouth of the wearer, said shield having a smooth concave inner surface, said shield having a post affixed to the middle portion of the outer surface and extendable through the lips of the wearer for receiving an appliance holding means on the exposed end; and
   a wire crosspiece disposed across said shield along a line forming a secant of the curvature of said shield, said crosspiece having a pair of straight end portions disposed generally on a central plane of said shield that is oriented horizontally when said appliance is worn by an upright wearer, each of said end portions having an end mounted in said inner surface of said shield, said end portions extending inwardly from said inner surface along said secant line, said crosspiece having a central portion intermediate said end portions and lying on said secant line, said central portion having a generally sinusoidal configuration including at least one central generally U-shaped bend extending in one direction with a generally U-shaped bend on either side thereof extending in an opposite direction, said central portion lying in a single plane containing said secant line and normal to said central plane with said U-shaped bends extending in opposite directions in said single plane, said crosspiece serving to hold back the tip of the tongue by means of said central portion when said appliance is worn.

2. The appliance according to claim 1 wherein said central portion has a pair of U-shaped bends extending in one direction with a U-shaped bend extending in the opposite direction intermediate the bends of said pair, and a U-shaped bend on either side of said pair of bends extending in the opposite direction.

3. The appliance according to claim 1 wherein said shield is made from a polystyrene plastic material, deformable upon heating for being fitted to the wearer and rigid at normal temperatures.

4. An appliance for prophylaxis and early orthodonic treatment of children, said appliance comprising:
   a curved, rigid shield of plastic material suitable for being inserted inside the lips and cheeks of the wearer and against the upper and lower dental arches containing the upper and lower teeth, said shield having a smooth, concave inner surface, said shield having a post fixed to the middle portion of an outer surface and extendable through the lips of the wearer for receiving an appliance holding means on the exposed end; and
   a strip on said inner surface of said shield extending normal to said inner surface on both sides of a central plane that is vertical when said appliance is worn by an upright wearer, said strip extending along said inner surface in an arcuate form corresponding to the lower dental arch, said strip having a downwardly extending flange at the inner edge thereof that fits behind the lower teeth of the wearer when said appliance is worn.

5. The appliance according to claim 4 wherein said flange lies at an obtuse angle with respect to said strip.

6. The appliance according to claim 4 wherein said strip and flange occupy an arc limited to approximately 90° on said inner surface of said shield.

7. The appliance according to claim 5 wherein said strip and flange occupy an arc limited to approximately 90° on said inner surface of said shield.

8. The appliance according to claim 4 wherein said shield is made from a polystyrene plastic material, deformable upon heating for being fitted to the wearer and rigid at normal temperatures.

* * * * *

UNITED STATES PATENT AND TRADEMARK OFFICE
CERTIFICATE OF CORRECTION

PATENT NO. : 4,690,640
DATED : September 1, 1987
INVENTOR(S) : Rolf Hinz

It is certified that error appears in the above-identified patent and that said Letters Patent is hereby corrected as shown below:

On the title page inventor should read

--(76) Inventor: Rolf Hinz --.

Signed and Sealed this

Nineteenth Day of January, 1988

Attest:

DONALD J. QUIGG

*Attesting Officer*

*Commissioner of Patents and Trademarks*